(12) United States Patent
Glenn et al.

(10) Patent No.: US 10,346,966 B2
(45) Date of Patent: Jul. 9, 2019

(54) NON-DESTRUCTIVE INSPECTION METHODS AND SYSTEMS

(71) Applicant: HALLIBURTON ENERGY SERVICES, INC., Houston, TX (US)

(72) Inventors: Corbin Sean Glenn, Burleson, TX (US); Zhenyu Xue, Sugar Land, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 7 days.

(21) Appl. No.: 15/527,684

(22) PCT Filed: Dec. 18, 2014

(86) PCT No.: PCT/US2014/071022
§ 371 (c)(1),
(2) Date: May 17, 2017

(87) PCT Pub. No.: WO2016/099497
PCT Pub. Date: Jun. 23, 2016

(65) Prior Publication Data
US 2018/0322622 A1    Nov. 8, 2018

(51) Int. Cl.
*G06T 7/00*    (2017.01)
*G01V 5/04*    (2006.01)
(Continued)

(52) U.S. Cl.
CPC .......... *G06T 7/0004* (2013.01); *E21B 43/117* (2013.01); *E21B 43/267* (2013.01);
(Continued)

(58) Field of Classification Search
None
See application file for complete search history.

(56) References Cited

U.S. PATENT DOCUMENTS 6,813,376 B1 * 11/2004 Hennessey ......... G01N 21/9501
257/E21.53
8,131,107 B2 * 3/2012 Sun ..................... G06K 9/6298
382/228
(Continued)

FOREIGN PATENT DOCUMENTS

WO    2013/058859    4/2013

OTHER PUBLICATIONS

PCT International Preliminary Report on Patentability, dated Dec. 23, 2016, Appl No. PCT/US2014/071022, "Non-Destructive Inspection Methods and Systems," Filed Dec. 18, 2014, 20 pgs.
PCT International Search Report and Written Opinion, dated Aug. 21, 2015, Appl No. PCT/US2014/071022, "Non-Destructive Inspection Methods and Systems," Filed Dec. 18, 2014, 15 pgs.

*Primary Examiner* — Delomia L Gilliard
(74) *Attorney, Agent, or Firm* — Gilliam IP PLLC

(57) ABSTRACT

A non-destructive inspection method that comprises obtaining one or more images corresponding to an X-ray, scanning electron microscope, or CT scan of an object, assigning numeric values to pixels of the images, comparing the numeric values to reference numeric values, and identifying an anomaly in the object based on the comparison. A non-destructive inspection system that comprises at least one processor, a memory in communication with the processor and storing instructions that causes the processor to obtain an image corresponding to an X-ray, scanning electron microscope, or CT scan of an object, assign numeric values to pixels of the image, compare the assigned numeric values to reference numeric values, and identify an anomaly in the object based on the comparison.

21 Claims, 10 Drawing Sheets

(51) Int. Cl.
*G01V 5/12* (2006.01)
*G01N 23/04* (2018.01)
*G06T 7/90* (2017.01)
*E21B 43/117* (2006.01)
*E21B 47/00* (2012.01)
*F42B 35/00* (2006.01)
*E21B 43/267* (2006.01)
*F42B 33/02* (2006.01)

(52) U.S. Cl.
CPC .......... *E21B 47/0002* (2013.01); *F42B 35/00* (2013.01); *G01N 23/04* (2013.01); *G01V 5/04* (2013.01); *G01V 5/12* (2013.01); *G06T 7/90* (2017.01); *F42B 33/025* (2013.01); *F42B 33/0214* (2013.01); *G06T 2207/10061* (2013.01); *G06T 2207/10081* (2013.01); *G06T 2207/10116* (2013.01)

(56) References Cited

U.S. PATENT DOCUMENTS

| | | | |
|---|---|---|---|
| 2003/0118230 | A1 | 6/2003 | Song et al. |
| 2004/0165760 | A1* | 8/2004 | Veneruso .............. G06T 7/0004 382/141 |
| 2011/0271751 | A1 | 11/2011 | Brooks et al. |
| 2012/0303309 | A1* | 11/2012 | Stuke ................... G01N 23/046 702/113 |
| 2013/0163720 | A1* | 6/2013 | Silva Ferreira ...... G01N 23/046 378/62 |
| 2014/0200831 | A1 | 7/2014 | Smith et al. |
| 2014/0282624 | A1* | 9/2014 | Holt ....................... G06F 9/542 719/318 |
| 2015/0302568 | A1* | 10/2015 | Hirai .................. G01N 23/2254 382/149 |

\* cited by examiner

380

390

NON-DESTRUCTIVE INSPECTION METHODS AND SYSTEMS

BACKGROUND

Explosive pellets are used downhole to fracture rock formations and thereby enhance petroleum recovery. It is difficult to machine an explosive pellet due to its complex shape, brittleness, and concerns about safety. Therefore, pellets are often manufactured by pressing explosive powder in a mold to form a solid pellet. Control of the density distribution of the pellet is critical for optimal performance. Specifically, concentricity of the distribution and consistent longitudinal distribution of the powder from one pellet to the next are the two main characteristics governing the performance of the pellet.

It is very difficult to determine the extent of pellet performance after detonation in a wellbore. Thus, a particular pellet configuration must be carefully designed, manufactured, and tested before deployment. Past inspection techniques include employing physical inspections, scanning electron microscopes, and X-ray scanning technology. Both scanning electron microscopes and X-ray technologies have limitations as the resultant images are grey-scale images containing details not discernable to the human eye yet important to pellet performance. It is thus difficult to isolate and identify faults within a given explosive pellet batch due to either manufacturing faults or design anomalies.

BRIEF DESCRIPTION OF THE DRAWINGS

Accordingly, there are disclosed in the drawings and the following description non-destructive inspection methods and systems.

Figure 1:
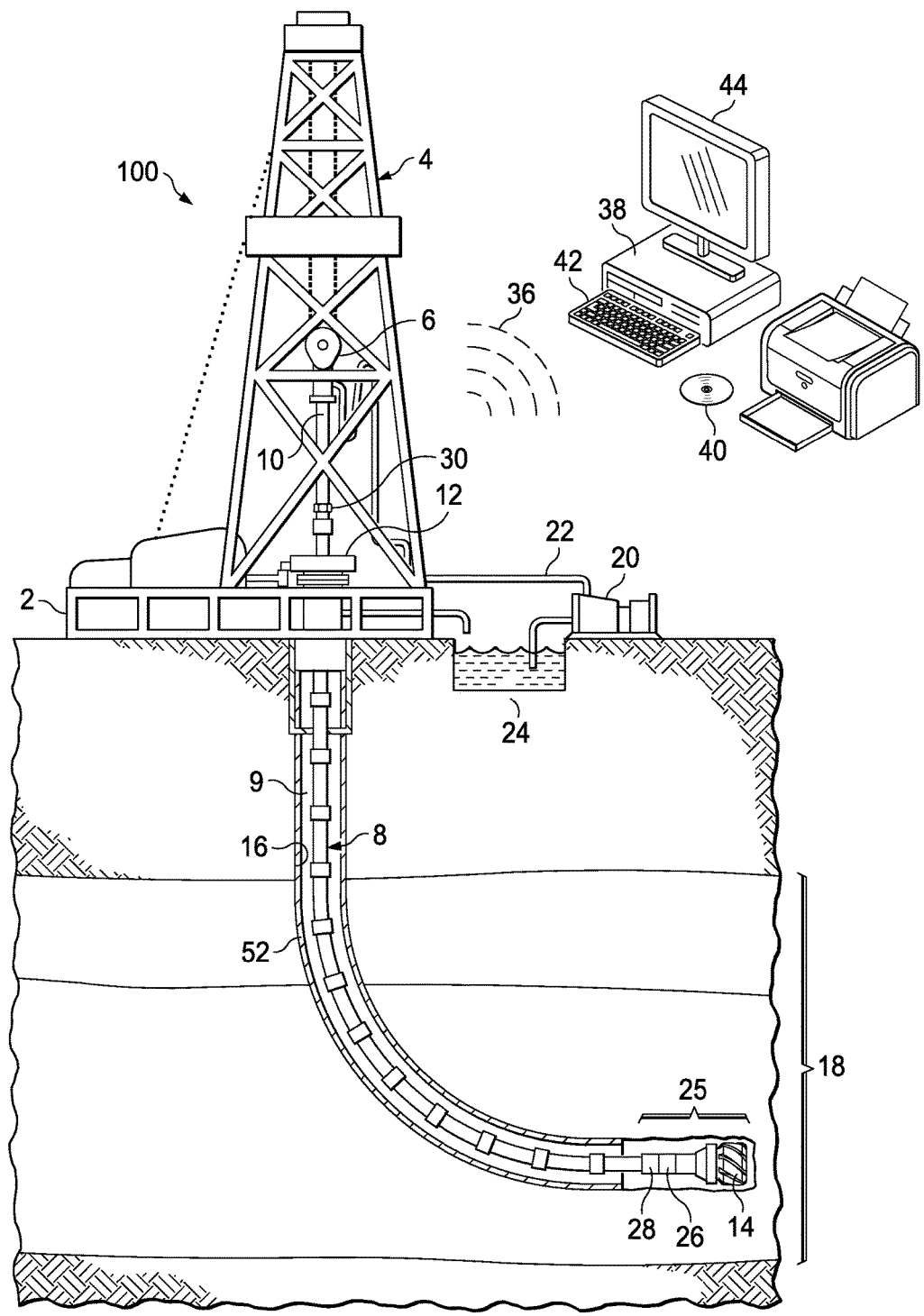
FIG. 1 is a schematic of an exemplary drilling operation.

It should be understood, however, that the specific embodiments given in the drawings and detailed description thereto do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

The present disclosure is directed to non-destructive inspection methods and systems. In at least some embodiments, the disclosed method and systems involve analysis of X-ray, scanning electron microscope (SEM), or X-ray computed tomography ("CT") scans or images, where numerical analysis is performed to distinguish between minor color variations in the images that are not detectable to the human eye. As used herein, "numerical analysis" refers to the use of a number range to represent a color scale. For example, if the color scale of an X-ray, SEM, or CT scan potentially has up to 65,000 different colors or grey-scales, a corresponding numerical analysis may involve assigning a number value between 0 and 64,999 to pixels of an image. For grey-scale images, a low number value (e.g., 0) may correspond to a darkest black pixel while a high number value (e.g., 64,999) corresponds to a brightest white pixel.

In at least some embodiments, a non-destructive inspection method includes obtaining an image corresponding to an X-ray, SEM, or CT scan of an object. The method also includes assigning numeric values to at least some pixels of the image, the numeric values corresponding to color scale values. The method also includes comparing at least some of the assigned numeric values to reference numeric values. The method also includes identifying an anomaly in the object based on the comparison. A related system includes at least one processor and a memory in communication with the at least one processor. The memory stores instructions that, when executed, causes the at least one processor to obtain an image corresponding to an X-ray, SEM, or CT scan of an object. The instructions, when executed, also cause the at least one processor to assign numeric values to at least some pixels of the image, the numeric values corresponding to color scale values. The instructions, when executed, also cause the at least one processor to compare at least some of the assigned numeric values to reference numeric values. The instructions, when executed, also cause the at least one processor to identify an anomaly in the object based on the comparison. Various image analysis options, calibration options, and object anomalies are described herein.

In at least some embodiments, the scanned object to be analyzed corresponds to an explosive pellet made from powder for use in well perforating operations. In such case, the disclosed methods and systems enable identification of anomalies corresponding to voids, fissures, density gradients, etc., in a pellet that could cause unwanted degradation of pellet performance downhole. Advantageously, the use of numerical analysis allows detection of anomalies that are not discernible to the naked eye. While the disclosed methods and systems were developed for use with explosive pellet inspection it should be appreciated that other objects (e.g., printed circuit boards or semiconductor materials) could be inspected using similar methods and systems.

As will be explained in greater detail herein, explosive pellets may be deployed in a downhole setting to improve fluid flow in a region of interest. FIG. 1 shows an illustrative drilling environment 100 for forming a borehole 16. In FIG. 1, a drilling platform 2 supports a derrick 4 having a traveling block 6 for raising and lowering a drill string 8. A drill string kelly 10 supports the rest of the drill string 8 as it is lowered through a rotary table 12. The rotary table 12 rotates the drill string 8, thereby turning a drill bit 14. Additionally or alternatively, rotation of the drill bit 14 is controlled using a mud motor or other rotation mechanism. As the drill bit 14 rotates, it creates a borehole 16 (represented using dashed lines) that passes through various formations 18. A pump 20 circulates drilling fluid through a feed pipe 22 to the kelly 10, downhole through the interior of drill string 8, through orifices in the drill bit 14, back to the surface via the annulus 9 around the drill string 8, and into a retention pit 24. The drilling fluid transports cuttings from the borehole 16 into the retention pit 24 and aids in maintaining the integrity of the borehole 16.

The drill bit 14 is just one piece of a bottom-hole assembly 25 that includes one or more drill collars 26 and logging tool 28. Drill collars 26 are thick-walled steel pipe sections that provide weight and rigidity for the drilling process. The logging tool 28 (which may be built into one of the drill collars) gathers measurements of various drilling or formation parameters. Without limitation, logging tool 28 may be integrated into the bottom-hole assembly 25 near the bit 14 to collect measurements. The collected measurements may be plotted and used for steering the drill string 8, monitoring drilling performance, and/or to analyze formation properties.

Measurements from the logging tool 28 can be acquired by a telemetry sub (e.g., integrated with logging tool 28) to be stored in internal memory and/or communicated to the surface via a communications link. Mud pulse telemetry is one common technique for providing a communications link for transferring logging measurements to a surface receiver 30 and for receiving commands from the surface, but other telemetry techniques can also be used.

The telemetry signals are supplied via a wired or wireless communications link 36 to a computer 38 or some other form of a data processing device. Computer 38 operates in accordance with software (which may be stored on information storage media 40) and user input via an input device 42 to process and decode the received signals. The resulting telemetry data may be further analyzed and processed by computer 38 to generate a display of useful information on a computer monitor 44 or some other form of a display device including a tablet computer. For example, an operator could employ this system to obtain and monitor drilling parameters or formation properties.

In the drilling environment 100 of FIG. 1, some well completion operations, including installation of a casing 52 representing at least one casing section, have been performed. Installation of each casing section involves joining modular casing segments until a desired casing section length is reached and/or lowering the casing section to a desired position in borehole 16. Once a desired length and position for a particular casing section is achieved, cementing operations are performed, resulting in a permanent casing section installation. As needed, the borehole 16 is extended by drilling through cement at an installed casing section terminus. The process of installing casing sections and extending 16 borehole can be repeated as desired. During drilling and/or well completion operations, the drill string 8 is routinely removed from the borehole 16, optionally reconfigured, and put back into the borehole 16 to continue the drilling process. After casing has been installed in a borehole such as borehole 16, perforating operations can be performed using explosive pellets that have been inspected using the non-invasive inspection methods and systems described herein.

Figure 2A:
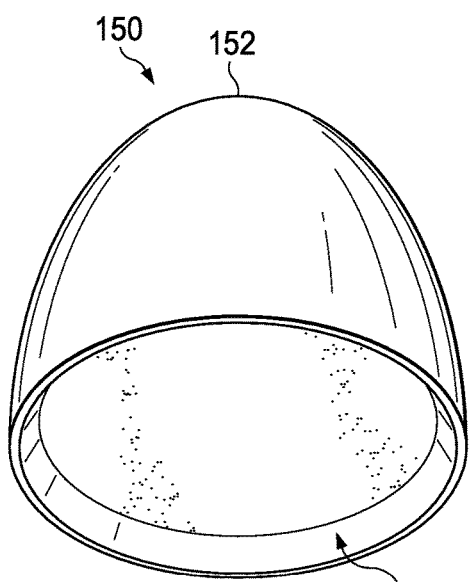
FIGS. 2A, 2B, and 2C are isometric views of an illustrative explosive pellet.

FIG. 2A is an illustrative isometric view of an explosive pellet 150 for use in creating fractures in a downhole formation. The pellet 150 has an apex 152 and an open end 154. The pellet 150 is constructed by taking a powdered explosive material, adding a binder, placing the powder mixture in a cast, and compressing the powder with a press to form a solid pellet. The composition of the explosive/binder mix and the physical shape of the cast may be changed to meet design goals for a particular application. Using a press to create an explosive pellet 150 avoids the need to use traditional machining and allows complex shapes to be created relatively easily.

Figure 2B:
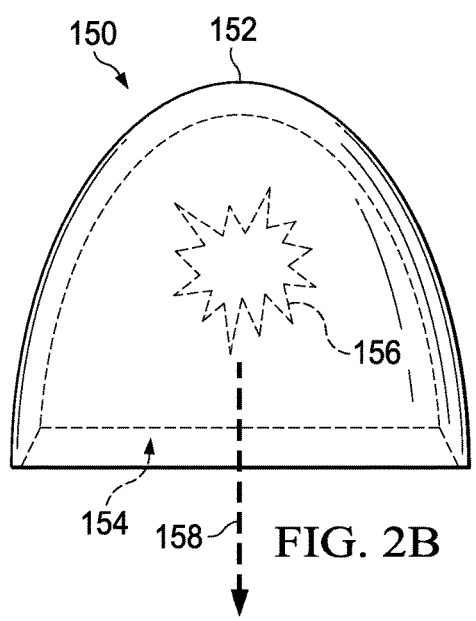

FIG. 2B is an illustrative side view of the explosive pellet 150 and is but one embodiment showing a thin-walled open-ended cone-like structure. Other embodiments are possible. In this configuration, when the pellet 150 is detonated beginning at the pellet's apex 152, an explosive force 156 is formed and focused towards and past an open end of the pellet 154, thus creating a high-velocity directional "jet" 158. The jet 158 can be used to burst through a casing wall and perforate the surrounding formation.

Figure 2C:
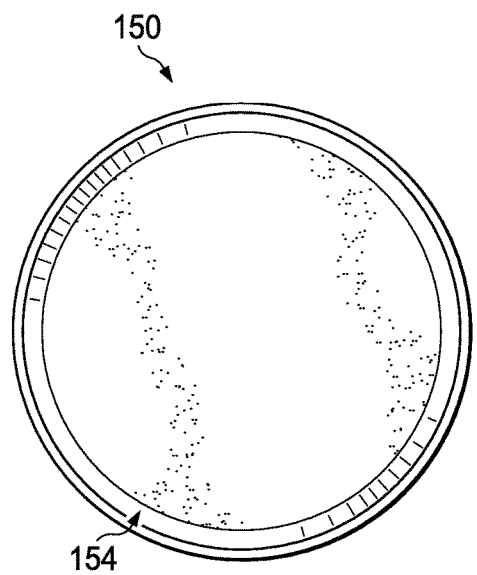

FIG. 2C is an illustrative end view of a pellet 150 showing the open end 154.

Figure 3A:
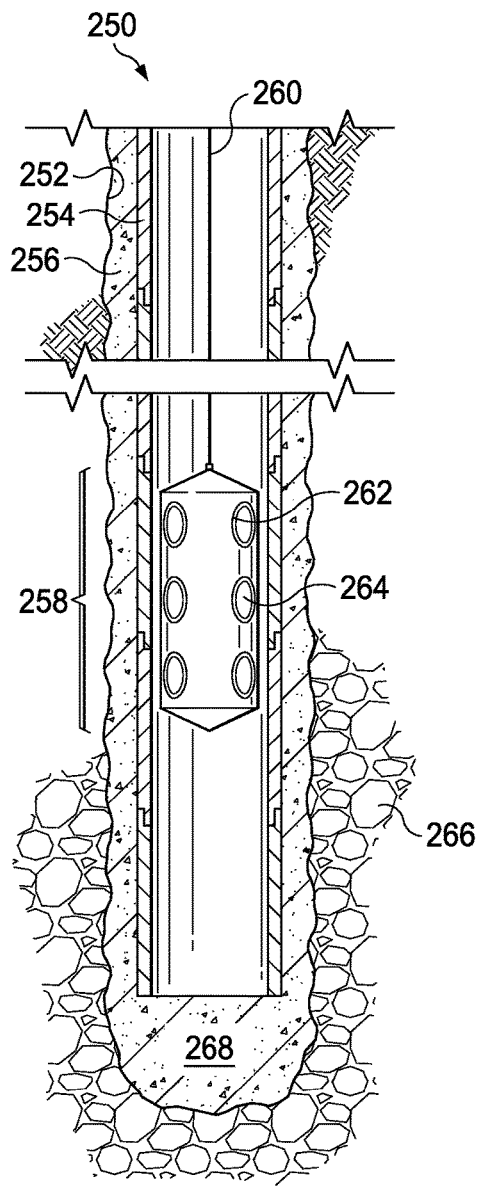
FIGS. 3A and 3B are illustrative schematic views of a perforating operation in a wellbore.

FIG. 3A is an illustrative schematic diagram of a perforating operation 250 in a wellbore environment. For the perforating operation 250, a wellbore 252 in a formation of rock 266 is represented as well as a plurality of casing segments 254. Also represented for the perforating operation 250 are an annulus 256 corresponding to the space between the casing 254 outer surface and the wellbore 252, cement 268 located in the annulus 256, a perforating tool 258, a wire or cable 260, a plurality of liners 262, and a plurality of explosive pellets 264. During wellbore construction, the wellbore 252 is drilled into the formation 266 to a desired location/depth. Once at the desired location, a series of casing segments 254 are assembled to form a casing string and are positioned downhole in the wellbore 252. Once the casing string 254 is in place, cement 268 is placed in the annulus 256 and cured to fixably attach the casing string 254 to the wellbore 252. The cured cement 268 helps to maintain wellbore pressure and retain fluids and gasses from passing between the formation 266 and the exterior of the casing string 254. After the cement 268 is in place and cured, a perforating tool 258 is lowered into the wellbore 252 via a wire or cable 260 controlled at the surface of the earth. In an alternative embodiment, the perforating tool 258 is part of a bottom-hole assembly (not shown). The perforating tool 258 includes a series of liners 262 that face outwards towards the inner wall of the casing string 254. In at least one of the liners 262, an explosive pellet 264 is fixably placed. The design and orientation of the perforating tool 258 places the explosive pellets 264 in close association with the interior wall of the casing string 254, with each explosive pellet's open end (154 in FIG. 2A) facing outward radially from the center of the casing string 254.

Figure 3B:
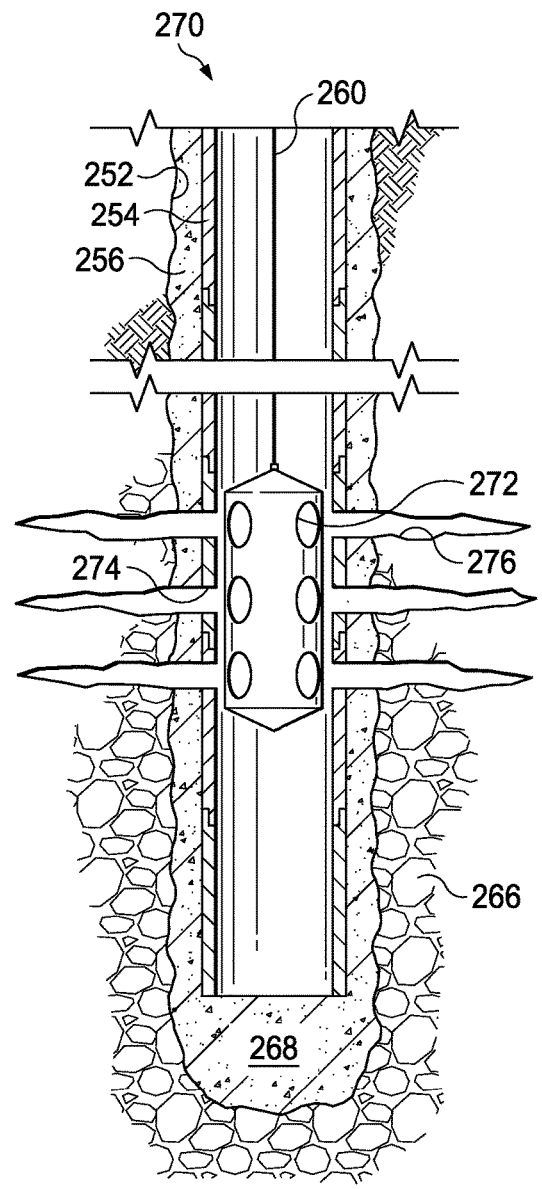

FIG. 3B is an illustrative schematic diagram of a completed perforating operation 270 after detonation of the explosive pellets. The diagram in FIG. 3B employs the same components as the diagram seen in FIG. 3A but includes empty liners 272, perforations 274 through the casing string 254, and fissures 276 in the formation. The fissures 276 allow fluids and gasses to flow from the surrounding formation 266 into the interior of the casing string 254. The explosive pellets (264 in FIG. 3A), once detonated, produces a focused jet of force outwards against the interior wall of the casing string 254, piercing the casing string 254 with a perforation 274 approximately ¼ to 1 inch in diameter, and further penetrating the formation 266 to a depth of 6 to 12 inches or more, depending on the composition of both the pellet (264 in FIG. 3A) and the formation 266. This process is known as perforating the formation and results in greatly increasing the potential flow rate of fluids and gasses from the pierced formation 266 towards the interior of the casing string 254. The perforations 274 are ports in fluid communication from the formation 266 to the interior of the casing string 254 and allows the flow of fluids and gasses through the casing string 254.

Other embodiments are possible when using explosive pellets in the aforementioned methods and systems. One such embodiment is employing exploding pellets to create fractures in a wellbore environment that has not been cased with a casing string or cemented, also known as an "open hole". In such an open hole environment, explosive pellets would be used to fracture the nearby rock formations to enhance fluid flow.

Another embodiment employed in wellbore operations is "overbalance perforations" where wellbore fluid is driven by an explosive force into the perforation. The selection of wellbore fluid has a direct effect on the performance of the perforations. Using clean wellbore fluids, free of crushed formation material, liner particles, case material, pipe dope, or mud can enhance fluid flow while using contaminated wellbore fluids may hinder formation fluid flow due to the clogging action of the particulates forced into the formation by the explosive force of the pellets.

In accordance with at least some embodiments, non-invasive methods and systems are used to inspect explosive pellets before their deployment downhole. The non-invasive methods and systems involve analysis of X-ray, SEM, or CT scans or images of a pellet to find anomalies below the surface of the pellet and/or anomalies too small to be seen. The images obtained from X-ray, SEM, or CT scans are a function of the amount of electromagnetic rays passing through a sample object onto the detector (or film), which produces variations in the image in the form of a grey-scale color. While some anomalies can be detected visually by the human eye and/or by scaling an image, the detection of other anomalies involves numerical analysis of X-ray, SEM, or CT images.

In at least some embodiments, numerical analysis of grey-scale images is performed to detect and isolate anomalies in the underlying structure or a scanned object, including cracks, voids, cold joints, or other imperfections. To perform numerical analysis, the grey-scale colors of image pixels are converted into numeric values corresponding to a scale (e.g., 0 to 64,999) representative of the grey-scale resolution of the images. Once numerical values are assigned to at least some image pixels, the resultant data can be analyzed in several ways depending on what the operator is interested in, i.e. density, particle distribution, the presence of contaminants, porosity, etc. As desired, calibration of the numerical values can be performed to improve the accuracy and precision of the data analysis operations. With the disclosed methods and systems, a high level of control over the manufacturing and design process for explosive pellets is possible, with the ultimate goal being to create better-performing and more stable explosive pellet designs.

The X-ray, SEM, or CT scans of an object produces a set of very detailed images. In at least some embodiments, set of images corresponds to a series of "slices" with very fine resolution (e.g., each slice may be 50-100 microns thick). Thus, a completed scan of an object may contain hundreds of individual slices available for analysis. The slices may be analysis individually (a two-dimensional analysis) or together (a three-dimensional analysis). In at least some embodiments, each image from these scans corresponds to a grey-scale image that includes over 65,000 different shades of grey, with many shades of grey being indistinguishable from other shades to the human eye. To analyze one or more images, the grey-scale colors of each image are converted into corresponding numbers, where each number represents a different shade. While entire images or a set of images could be converted into a 2D or 3D matrix of numbers, it should be appreciated that analysis of an entire image or set of images is not required. Another option would be to select areas of an image or to select sub-volumes corresponding to a set of images for analysis. In either case, a set of numbers representing 2D or 3D X-ray, SEM, or CT scans are generated and stored for analysis. The set of numbers can be used, for example, to produce color distribution graphs corresponding to a particular area or volume of an object. A color distribution graph can be generated, for example, by binning each number or each sub-range of numbers and generating a corresponding plot of data that shows how many of each number or each sub-range of numbers are present in the particular area or volume being analyzed. In accordance with at least some embodiments, a software program enables various 2D or 3D analysis options. The analysis options may be selected, for example, via a user interface with different windows, menus, tabs, selectable buttons, etc.

Figure 4A:
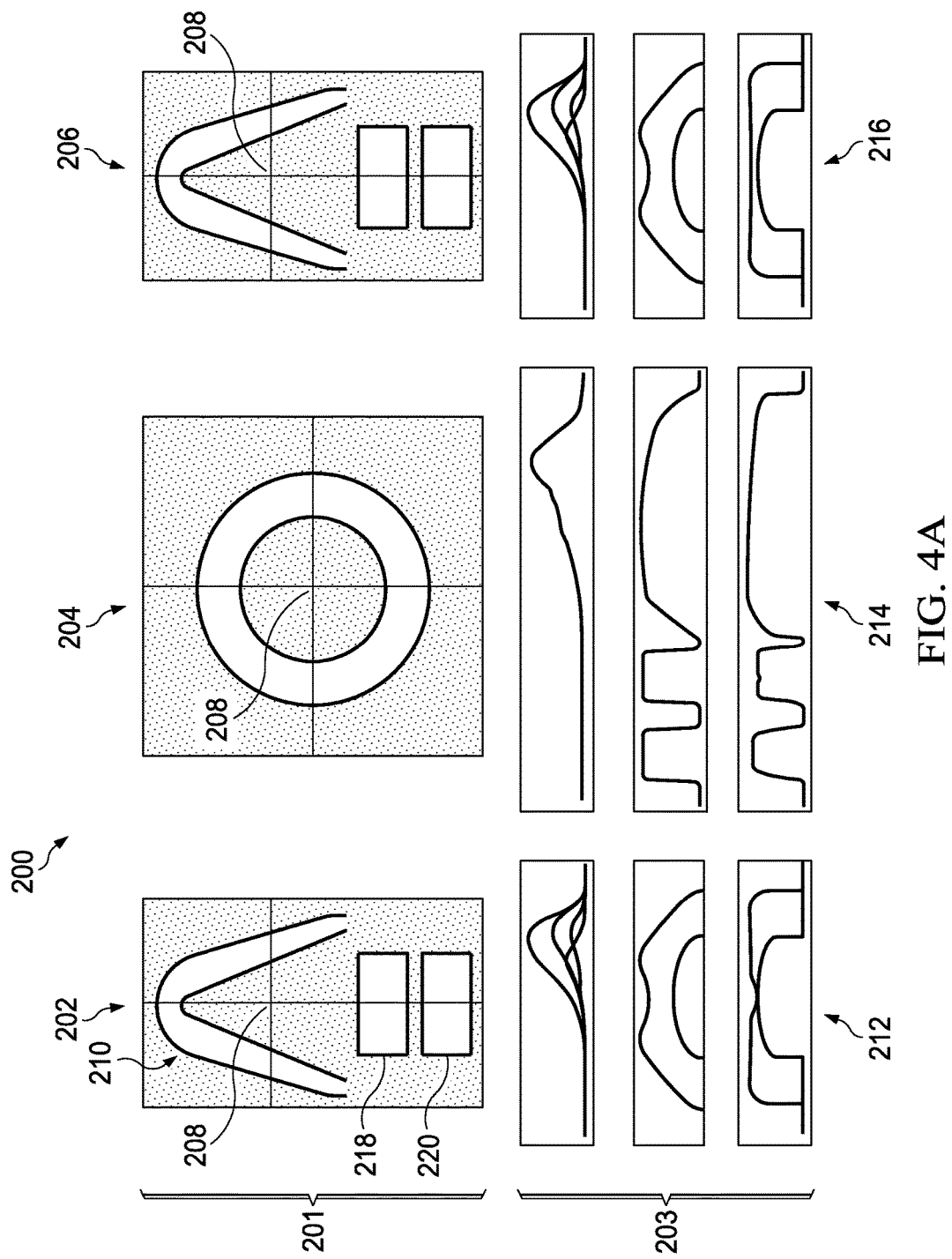
FIGS. 4A and 4B are images and graphs related to an illustrative ideal pellet.

One analysis tool for the operator is referred to herein as an "Inspection Screen." An example Inspection Screen displays a graphical image of the scanned object in three separate axis views (x, y, and z), where the operator can move a cursor to inspect any particular point, sub-area, or two-dimensional area of the pellet and see the values representing pixel color count, density, volume, and size. Furthermore, the operator can review the information displayed on the Inspection Screen to identify variations in density that may suggest a void, a crack, a "cold joint" (i.e., where the powder didn't fully mold with adjoining areas), or any other anomalous characteristics. FIG. 4A shows an example Inspection Screen 201 for an explosive pellet, and will later be described in greater detail. Another analysis tool is referred to herein as an "Analysis Screen." An example Analysis Screen displays line graphs of the scanned object to include displays of density and volume. Further, reference graphs or curves (e.g., a Gaussian curve) may be displayed in the Analysis Screen to enable comparison of an ideal curve with the analysis results. The operator may inspect the graphs corresponding to the analysis results for sudden changes in values that may suggest anomalies within the scanned object. For example, the operator may use the Analysis Screen to identify abrupt changes in the density gradient, where such changes in the density gradient correspond to fissures, cracks, voids, particle distribution, the presence of contaminants, cold joints, etc., that are often not discernible to the unaided human eye. The Analysis Screen also enables the operator to compare graphs obtained from a scanned object with graphs obtained from calibration disks or objects having a predetermined density, shape, and/or other characteristics. In this manner, the operator can identify whether the characteristics of the scanned object are acceptable or if the manufacturing, design, or composition of the scanned object will need to be changed.

The information presented on the Analysis Screen is obtained by performing one-, two-, or three-dimensional analysis of scanned object data (e.g., a matrix of numbers corresponding to colors) stored in a database. For example, in at least some embodiments, the Analysis Screen displays a pixel count of numeric data corresponding to the grey-scale shade of a scanned object. The pixel count is an important metric and may be represented in a histogram graph, with variations in pixel count values corresponding to variations in the density of the sample area or volume under analysis. A relatively narrow histogram graph of pixel count values means a relatively uniform distribution and uniformity of the scanned object. The pixel count value can also be used to derive the total volume of the scanned object. The pixel count also may provide information regarding density, mass, diameter, or height of the scanned object. In some embodiments, the mean value of all pixels in an area or volume may be used to estimate parameters of interest such as density or mass.

In the Analysis Screen, an operator may see anomalies directly or may otherwise detect them via numeric analysis. By using the cursor, the operator can review a single point, a two-dimensional plane, a sub-area, or an entire three-dimensional area within the scanned abject and see whether there are abrupt fissures, voids, cracks, cold joints, etc. Utilizing the Inspection Screen and the Analysis Screen together gives the operator a method for inspecting a scanned object so as to improve upon the manufacturing process and to ensure optimized performance of the pellets in a downhole environment. FIG. 4A shows an example Inspection Screen 203 for an explosive pellet and will later be described in greater detail.

In at least some embodiments, the numeric values applied to an area or volume of a scanned object may be calibrated (e.g., an offset may be applied to each numeric value as needed). Alternatively, information regarding a calibration object scanned at the same time and/or by the same scanner as an object to be inspected can be reviewed in the Inspection Screen or Analysis Screen to determine whether a scanned object has acceptable characteristics. In an example calibration, one or more calibration disks with known characteristics (e.g., a known density and composition) are scanned with the object to be inspected. For example, two calibration disks of a known density and composition may be scanned with the object to be inspected, where one of the calibration disks is less dense than a target density for the object to be inspected, while the other calibration disk in more dense than the target density of the object to be inspected. In an alternative embodiment, the calibration disk may have the same density as the target density of the object to be inspected. In yet another embodiment, the calibration object may be of a target pellet that has previously been established as having acceptable characteristics.

In one example embodiment, an X-ray, SEM, or CT scan is conducted of a pellet along with at least one calibration disk. To perform an analysis, an X-ray, SEM, or CT scan of the pellet is conducted, unwanted noise is removed from the resultant data, and the mean pixel value is calculated for both the pellet and the calibration disk. The calibration disk has a known density and volume and has been previously verified to be manufactured without faults. Since the disk is composed of a uniform monolithic powder of known density and volume, the disk's scan results may be compared to the pellet's scan results to reveal similarities and differences between the two.

After the scan and analysis of the pellet is completed, the operator can decide upon a number of choices, including but not limited to choosing a different explosive powder with different properties, accepting the results and doing nothing further, selecting a new powder flow rate, changing the geometry of the pellet, changing the pressure of the press used during pellet manufacturing (currently 1 lb. of pressure), changing the binder, or changing the liner composition or shape.

A further analysis step which may be performed involves analysis of X-ray, SEM, or CT scans of a pellet liner that mechanically holds the explosive pellets in a downhole tool. The liners are similarly shaped to hold the explosive pellets and are made of metal. Being metal, and thus opaque to X-ray, SEM, and CT scans, the inspection of liners may be limited as internal details of the composition of the liner will not reveal any details. However, X-ray, SEM, or CT scans of lines may still enable detection of cracks, voids, contaminants, fissures, and other anomalies on the outside surface of the liner that not visible to the human eye.

FIG. 4A shows the Operator Screen 200 for analyzing the data from scanned objects. The Operator Screen 200 is comprised of an "Inspection Screen" 201 and an "Analysis Screen" 203. In this example, the object is an explosive pellet that has been scanned and will be inspected and analyzed. The Inspection Screen 201 shows a diagram of a "good" pellet used to present the analysis data to an operator for inspection. Each object scanned results in a three-dimensional collection of data associated with it. The sample data can be analyzed in x, y, and z-axis cross-section views (202, 204, and 206 respectfully) using a crosshair cursor 208 that selects which slice or "plane" to inspect. The crosshair cursor 208 may be moved to any part of each view 202, 204, and 206. By moving the cursor 208 around, the operator can review the data associated with that slice or plane as seen in the plotted data shown in graph sets 212, 214, and 216 as part of the Analysis Screen 203. These graph sets display the pixel count for each slice or plane selected by the cursor 208 and can display discontinuities in the object or differences in densities indicating a possible problem with the object.

The x-axis view scan 202 shows scan data of an explosive pellet 210 and two calibration disks 218, 220. Data from the scans are also presented as pixel count and density graphs in graph set 212. The y-axis view scan 204 is associated with graph set 214. Another view orthogonal to views 202 and 204 is the z-axis view 206 with associated graph set 216. From these graph sets 212, 214, and 216, an operator can determine if the pellet is of uniform density and without voids, cracks, or faults when compared to both an ideal uniform Gaussian curve and at least one calibration disk 218, 220.

Figure 4B:
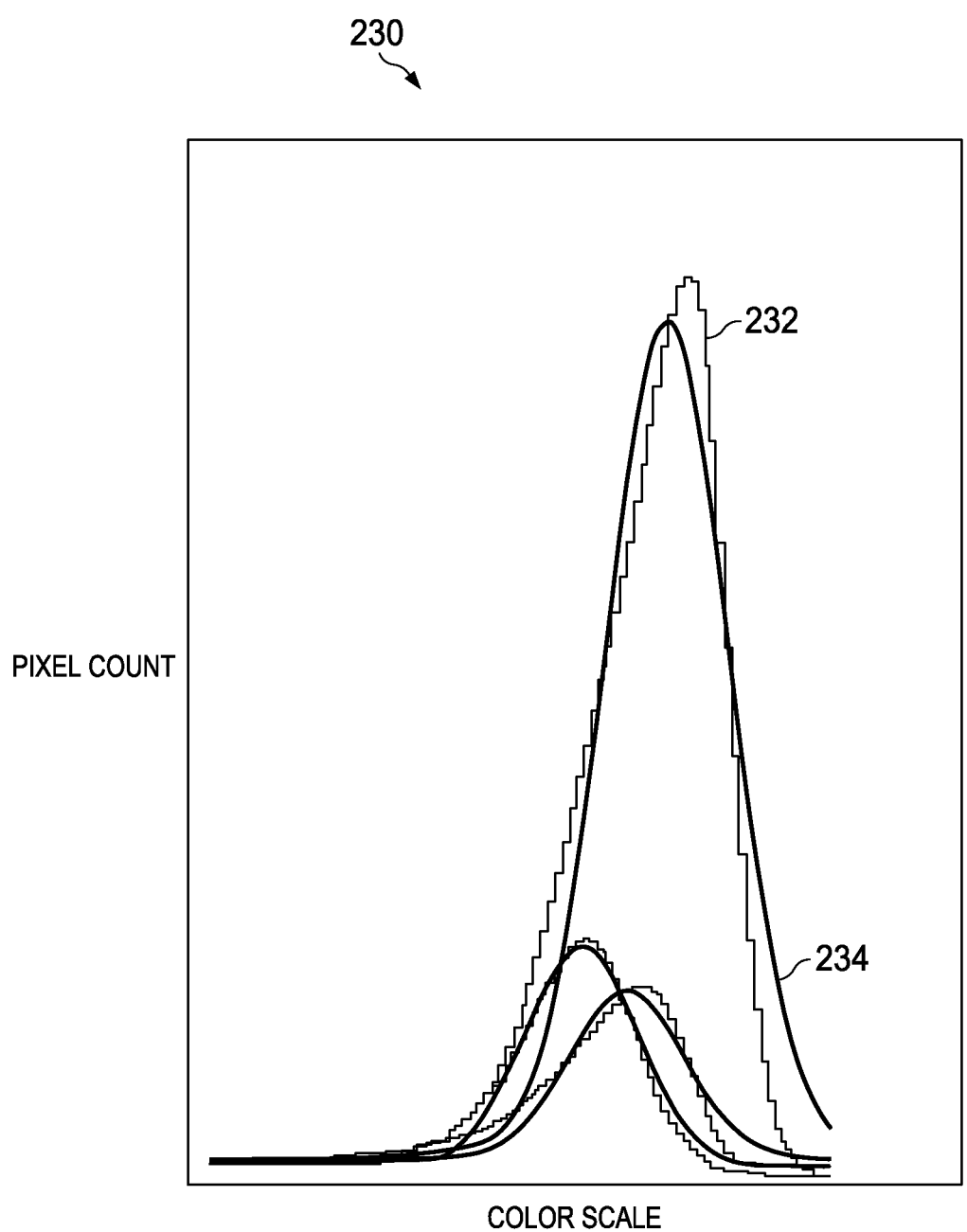

FIG. 4B shows an additional graph 230 containing several plots of data of a "good" pellet sampled data 232 (shown as a segmented curve). In addition to the plotted sampled data 232, an "ideal" Gaussian curve 234 (shown as a smooth curve) is displayed for reference. The operator or a computer process can compare the ideal curve 234 to the sampled data curve 232 to check for irregularities, gaps, inflections, etc. that could indicate design or manufacturing flaws. Additional curves in the graph 230 include plots of the calibration disks, which are used to compare a known good object to the data of the object being sampled.

Figure 5A:
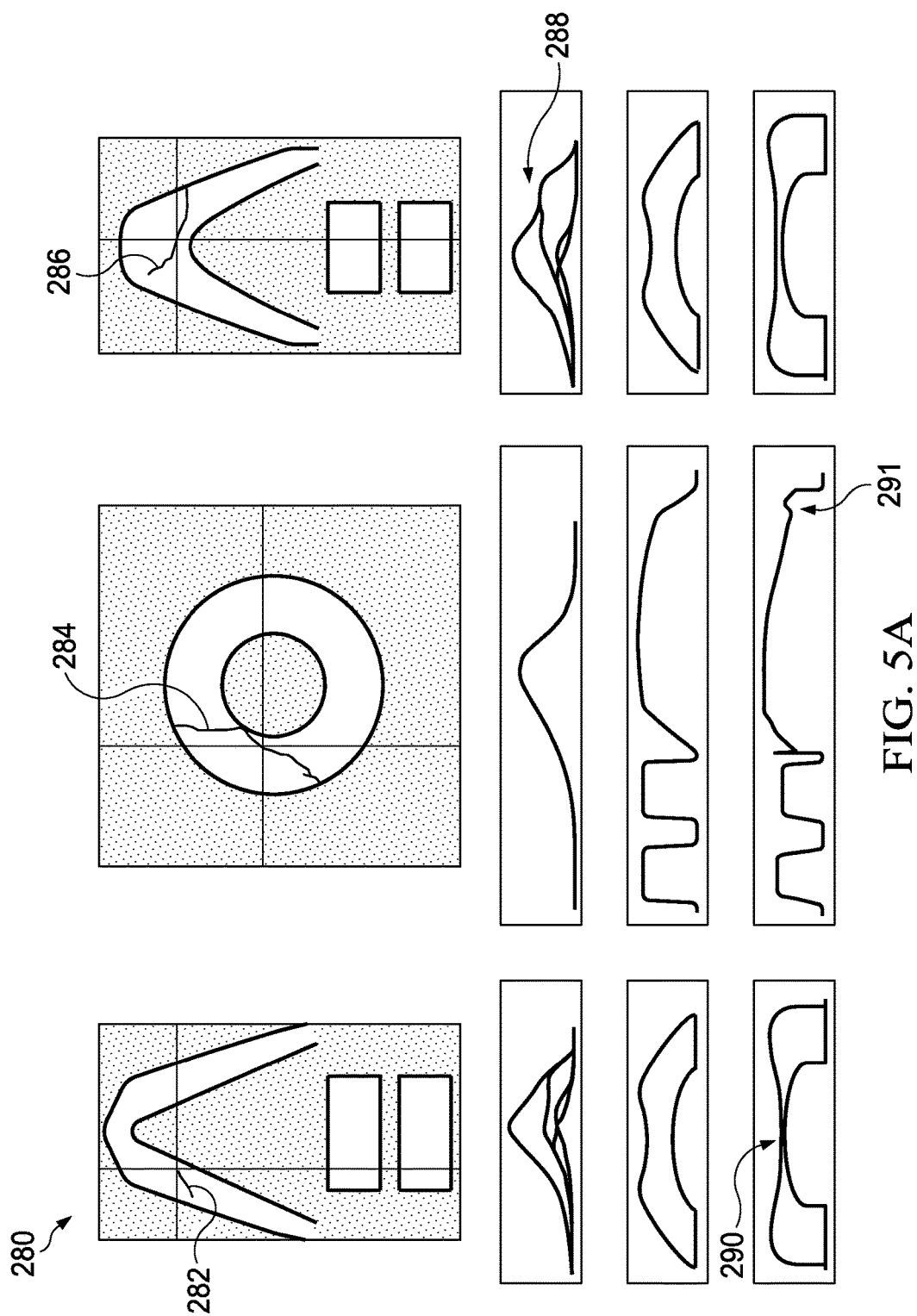
FIGS. 5A and 5B are images and graphs related to an illustrative defective pellet.

FIG. 5A shows a similar set of screens, diagrams, and graphs as seen in FIGS. 4A and 4B. In this embodiment, however, the good pellet is exchanged for a defective pellet containing cracks. In this analysis, a visual inspection of the Inspection Screen diagram of a defective pellet 280 shows a crack in the object in all three axis views. An operator can visually see a crack 282, 284, and 286 in the sample from viewed all three axis scans. In this example, the crack may or may not be visible using the human eye but is visible using the scanned data. Furthermore, the Analysis Screens also show anomalies in the pixel count and density graphs as compared to the calibration disks and the ideal Gaussian distribution graph. Anomalies 288, 290, and 291 are seen in the graph data.

Figure 5B:
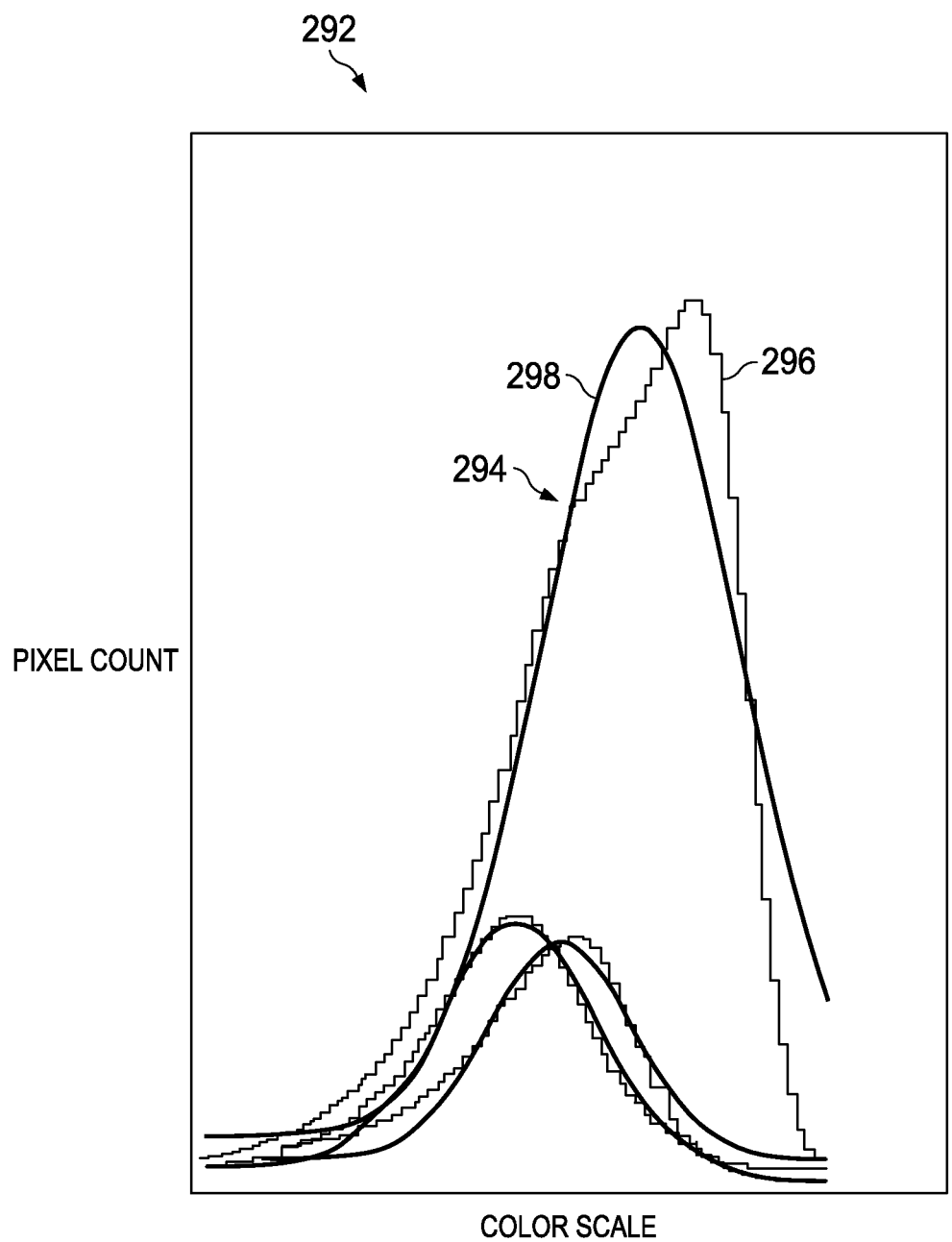

FIG. 5B are graphs 292 of a "defective" pellet sampled data 296 (shown as a segmented curve). In addition to the plotted sampled data 296, an "ideal" Gaussian curve 298 (shown as a smooth curve) is displayed for reference. The operator or a computer process can compare the ideal curve 298 to the sampled data curve 296 to check for irregularities, gaps, inflections, etc. that could indicate design or manufacturing flaws. In this embodiment, a distinct deviation from the desired curve is shown at point 294 along the ideal curve 298. Additional curves in the graph 292 include graphs of the calibration disks.

Figure 6A:
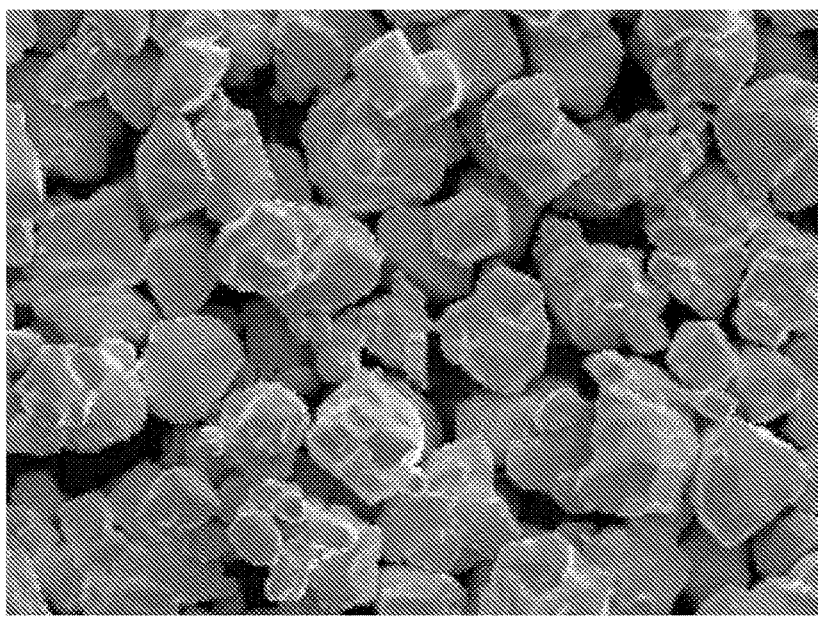
FIGS. 6A and 6B are illustrative images from a scanning electron microscope.
Figure 6B:
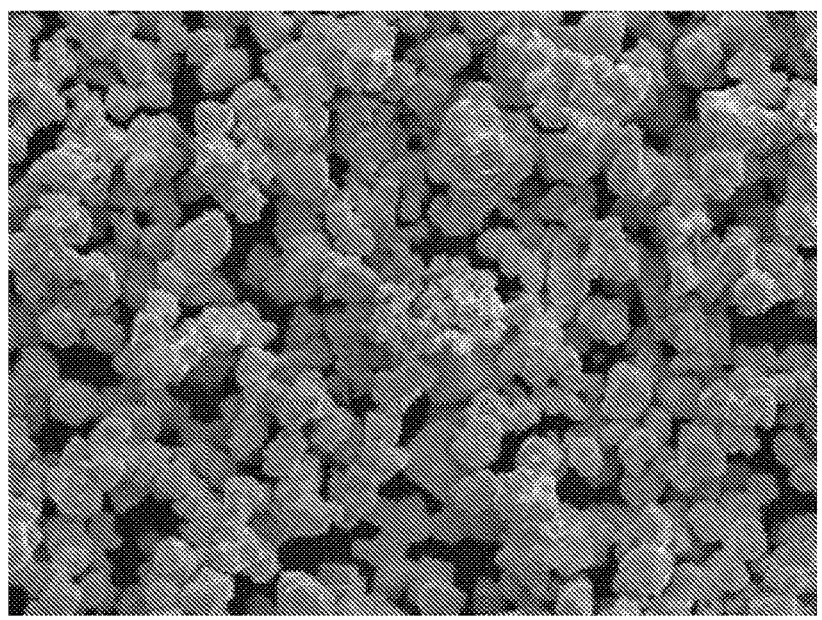

FIGS. 6A and 6B show two illustrative scanning electron microscope (SEM) images 380, 390 of two different sample materials. In both images 380, 390 the sample material has been magnified 500 times. The images 380, 390 are grey scale images that can be processed and analyzed by the methods and systems seen in this disclosure.

Figure 7:
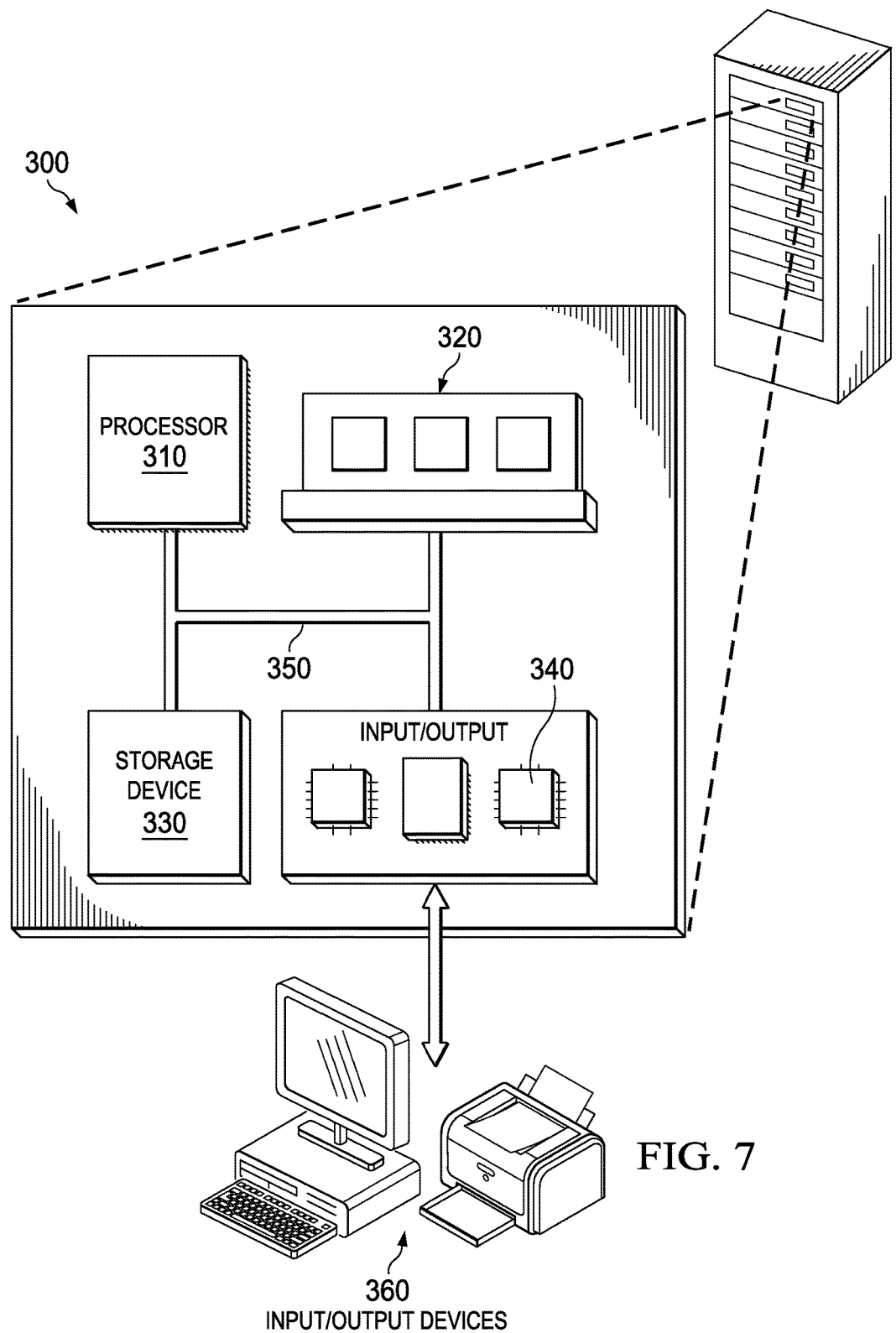
FIG. 7 is a block diagram of an illustrative processing system.

FIG. 7 shows an illustrative processing system 300. The system 300 may correspond to the computer system 38 mentioned in FIG. 1 and/or another computer system involved with obtaining input parameters or obtaining scanned pellets log data to inspect pellet design and manufacturing techniques or to perform other tasks as described herein. Based on these analyses, the operator may proceed with fracturing operations, modify pellet design and manufacturing, or reject failed samples as well as record the history of pellet production to see trends over time.

The system 300 includes a processor 310, a memory 320, a storage device 330, and an input/output device 340. Each of the components 310, 320, 330, and 340 can be interconnected, for example, using a system bus 350. The processor 310 is capable of processing instructions for execution within the system 300. In some embodiments, the processor 310 is a single-threaded processor, a multi-threaded processor, or another type of processor. The processor 310 is capable of processing instructions stored in the memory 320 or on the storage device 330. The memory 320 and the storage device 330 can store information within the computer system 300.

The input/output device 340 provides input/output operations for the system 300. In some embodiments, the input/output device 340 can include one or more network interface devices, e.g., an Ethernet card; a serial communication device, e.g., an RS-232 port; and/or a wireless interface device, e.g., an 802.11 card, a 3G wireless modem, or a 4G wireless modem. In some embodiments, the input/output device can include driver devices configured to receive input data and send output data to other input/output devices, e.g., keyboard, printer and display devices 360. In some embodiments, mobile computing devices, mobile communication devices, and other devices can be used.

In accordance with at least some embodiments, the disclosed methods and systems related to scanning and analyzing material may be implemented in digital electronic circuitry, or in computer software, firmware, or hardware, including the structures disclosed in this specification and their structural equivalents, or in combinations of one or more of them. Computer software may include, for example, one or more modules of instructions, encoded on computer-readable storage medium for execution by, or to control the operation of, a data processing apparatus. Examples of a computer-readable storage medium include random access memory (RAM) devices, read only memory (ROM) devices, optical devices (e.g., CDs or DVDs), and disk drives.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative, or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

Figure 8:
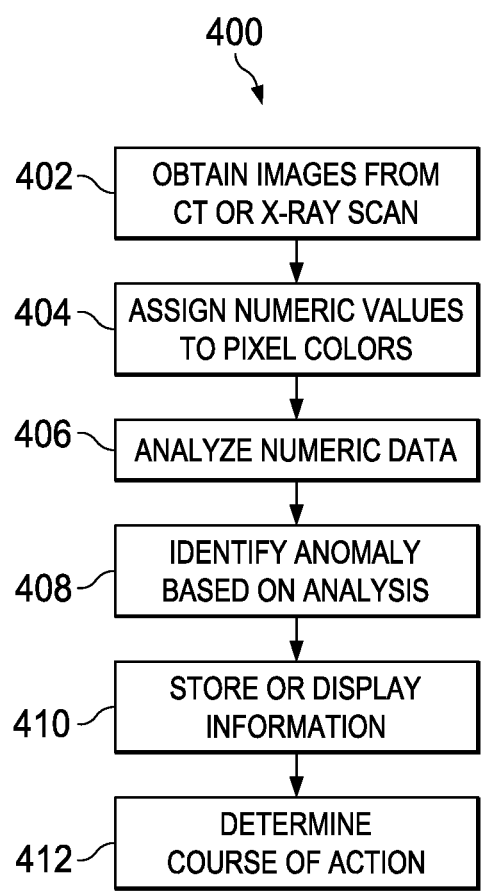
FIG. 8 is a flow chart for an object inspection process.

FIG. 8 presents an illustrative process 400 for inspecting an object for faults, fissures, voids, anomalies, density variation, etc. As described herein, the process 400 may be used for non-invasive inspection of an explosive pellet or for other objects. The process 400 may be implemented by computer 38 (FIG. 1) and/or another computer. At block 402, X-ray, SEM, or CT scans of an object is obtained. The scans correspond to images of layers or slices of the object with over 65,000 different shades of grey possible in each image. In at least some embodiments, the object at least one calibration disk may be scanned with the object for use in determining a baseline value for materials of known density, volume, and size.

At block 404, the image is converted to a numerical set of data corresponding to the colors represented in the image. For example, the conversion of block 404 may result in a matrix or database containing a representative value for each of the various gray shades found in the original image.

At block 406, the numerical data is analyzed and processed. For example, block 406 may involve removing unwanted noise from the set of data, calculating the mean values of numerical data for a given area or volume, obtaining a pixel count that represents the distribution of color values for a scanned area or volume. Unwanted noise may take the form of extraneous data located away from the object being scanned, any bias in the signal due to external factors, or any change in the data of the calibration disk which might warrant a correction to the data ("normalization").

Furthermore, a comparison may be performed on the scanned data to compare the assigned values of the object to data values from a scanned reference object or a stored reference data set. This comparison may be automated and performed by the processor (shown as item 310 in FIG. 7), or manually conducted by an operator using a display screen (shown as item 360 in FIG. 7). The operator could compare a histogram chart of the scanned object to a known reference object's histogram plot or refer to a data file to be used as a reference. The histogram plot may be of the entire object, a point in the object, a plane "slice" of the object, or a sub-area or area of the object under inspection.

Finally, an additional step of calibrating the data may be performed. The numerical data is calibrated using the known density of the calibration disks and/or other data available to the operators including past scans and operational experience. As the density and volume of the calibration disks are known values, comparisons of the known values with the measured values of the disks can be used to calibrate the process to ensure accuracy. Two calibration disks are used, each may be of the same or of a different material, density, volume of a combination of the three. When scanned and analyzed, the resultant values can be used as a known value comparison to the object being scanned. The calibration step seeks to align the scanned object's data set to a known data set to verify accuracy of the scan itself. This step may be performed automatically by the processor or manually by the operator. Calibration may be carried out by comparing the difference between the mean values of a known reference object or "goal" and an estimated target reference set of data. Any difference between the two sets of data would indicate a possible "out of alignment" condition and would invite a "correction" to future scans. The data in the calibration may be in the form of image values, pixel color count, or any other resultant data set available to the system or the operator for analysis.

At block 408, the object's scanned data is compared to known good data and anomalies can be discovered. Anomalies may take the form of sudden changes in the color images of the object or sudden changes in the various graph plots as shown in the Analysis Screen seen in FIG. 4B. Anomalies may also be discovered by viewing the Inspection Screen, seen in FIG. 4B and searching for discolorations, sudden changes in densities, etc. depending on the physical shape of the object being scanned.

At block 410, the calibrated data is stored and displayed. The inspection log is stored or displayed for use by an operator for immediate use or for use at a later date. In this manner, collected data of historical production runs may be compared to present-day manufacturing efforts to establish trends or baselines that may help the operator understand in interpreting the scanned data correctly.

At block 412, the operator may make a decision regarding the manufacturing process based on the data logs. The manufacturing process may proceed unchanged or the operator may modify the parameters of the explosive pellet design or manufacturing process. The parameters include, but are not limited to, changing the powder properties including burn rate, shape, composition, press pressure, binder, etc. of the powder to optimize a given process, a different flow rate when pressing the powder in the mold, a change in the geometry of the pellet, changing the pressure of the press (for example, from 1 lb. per square inch to 2 lbs. per square inch), or changing the binder. The operator may, for example, select to adjust controllable parameters so as to reduce the likelihood of manufacturing failures. In some embodiments, a controller can be controlled and/or manipulated automatically in accordance with the inspection log as compared to a predetermined set of reference values. Alternatively, recommendation to change parameters such as modifying the powder, press pressure, binder quantity, shape of the pellet, etc. may be presented to an operator in accordance with the inspection log.

Embodiments disclosed herein include:

A: a non-destructive inspection method that comprises: obtaining one or more images corresponding to an X-ray, SEM, or CT scan of an object; assigning numeric values to at least some pixels of the image, the numeric values corresponding to color scale values; comparing at least some of the assigned numeric values to reference numeric values; and identifying an anomaly in the object based on the comparison.

B: a non-destructive inspection system that comprises: at least one processor; a memory in communication with the at least one processor and storing instructions that, when executed, causes the at least one processor to: obtain an image corresponding to an X-ray, SEM, or CT scan of an object; assign numeric values to at least some pixels of the image, the numeric values corresponding to color scale values; and compare or display at least some of the assigned numeric values relative to reference numeric values to enable identification of an anomaly in the object.

Each of embodiments A and B may have one or more of the following additional elements in any combination: Element 1: further comprising: obtaining a plurality of images corresponding to X-ray, SEM, or CT scans of the object; assigning numeric values to at least some pixels of each image, the numeric values corresponding to color scale values; comparing at least some of the assigned numeric values to reference numeric values; and identifying a three-dimensional anomaly in the object based on the comparison. Element 2: wherein the anomaly corresponds to a density or porosity anomaly. Element 3: wherein the anomaly corresponds to a shape anomaly. Element 4: wherein the anomaly corresponds to a particle distribution anomaly. Element 5: wherein the anomaly corresponds to a contaminant anomaly. Element 6: further comprising displaying a message regarding the anomaly. Element 7: further comprising displaying a representation of the anomaly. Element 8: wherein the object is an explosive pellet for use in a downhole environment. Element 9: wherein the object is a liner for use in a downhole environment. Element 10: further comprising obtaining the reference numeric values from scanning a calibration disk at the same time as the object. Element 11: wherein the instructions, when executed, cause the at least one processor to: obtain a plurality of images corresponding to X-ray, SEM, or CT scans of the object; assign numeric values to at least some pixels of each image, the numeric values corresponding to color scale values; and compare or display at least some of the assigned numeric values relative to reference numeric values to enable identification of an anomaly in the object. Element 12: wherein the anomaly corresponds to a density or porosity anomaly. Element 13: wherein the anomaly corresponds to a shape anomaly. Element 14: wherein the anomaly corresponds to a particle distribution anomaly. Element 14: wherein the anomaly corresponds to a contaminant anomaly. Element 15: further comprising a monitor in communication with the processor, wherein the processor causes a message regarding the anomaly to be displayed via the monitor. Element 16: further comprising a monitor in communication with the processor, wherein the processor causes a representation of the anomaly to be displayed via the monitor. Element 17: wherein the object is an explosive pellet or liner for use in a downhole environment. Element 18: wherein the reference numeric values are associated with a calibration disk scanned at the same time as the object.

What is claimed is:

1. A non-destructive inspection method that comprises:
    obtaining a first image of an object, wherein the first image comprises at least one of an X-ray, SEM, or CT scan of the object;
    determining numeric values for one or more pixels of the first image based, at least in part, on a color scale resolution for the first image;
    calibrating the numeric values based, at least in part, on an image of a reference object;
    comparing one or more of the calibrated numeric values to reference numeric values; and
    identifying an anomaly in the object based, at least in part, on the comparison.

2. The method of claim 1, further comprising:
    obtaining a plurality of images of the object;
    determining numeric values for one or more pixels of each of the plurality of images based, at least in part, on a color scale resolution for the plurality of images;
    comparing one or more of the calibrated numeric values to reference numeric values; and
    identifying a three-dimensional anomaly in the object based on the comparison.

3. The method of claim 1, wherein the anomaly corresponds to a density or porosity anomaly.

4. The method of claim 1, wherein the anomaly corresponds to a shape anomaly.

5. The method of claim 1, wherein the anomaly corresponds to a particle distribution anomaly.

6. The method of claim 1, wherein the anomaly corresponds to a contaminant anomaly.

7. The method of claim 1, further comprising displaying a message regarding the anomaly.

8. The method of claim 1, further comprising displaying a representation of the anomaly.

9. The method of claim 1, wherein the object is an explosive pellet for use in a downhole environment.

10. The method of claim 1, wherein the object is a liner for use in a downhole environment.

11. The method of claim 1, further comprising obtaining the reference numeric values from scanning a calibration disk.

12. A non-destructive inspection system that comprises:
    a processor;
    a memory in communication with the processor and storing instructions that, when executed, causes the processor to:
        obtain a first image of an object, wherein the first image comprises at least one of an X-ray, SEM, or CT scan of the object;
        determine numeric values for one or more pixels of the first image based, at least in part, on a color scale resolution for the first image;
        calibrate the numeric values based, at least in part, on an image of a reference object; and
        compare one or more of the calibrated numeric values to reference numeric values to enable identification of an anomaly in the object.

13. The system of claim 12, wherein the instructions, when executed, cause the processor to:
    obtain a plurality of images of the object;
    determine numeric values for one or more pixels of each of the plurality of images based, at least in part, on a color scale resolution for the plurality of images; and
    compare display one or more of the calibrated numeric values to reference numeric values to enable identification of an anomaly in the object.

14. The system of claim 12, wherein the anomaly corresponds to a density or porosity anomaly.

15. The system of claim 12, wherein the anomaly corresponds to a shape anomaly.

16. The system of claim 12, wherein the anomaly corresponds to a particle distribution anomaly.

17. The system of claim 12, wherein the anomaly corresponds to a contaminant anomaly.

18. The system of claim 12, further comprising a monitor in communication with the processor, wherein the processor causes a message regarding the anomaly to be displayed via the monitor.

19. The system of claim 12, further comprising a monitor in communication with the processor, wherein the processor causes a representation of the anomaly to be displayed via the monitor.

20. The system of claim 12, wherein the object is an explosive pellet or liner for use in a downhole environment.

21. The system of claim 12, wherein the reference numeric values are associated with a scanned calibration disk.

* * * * *